United States Patent
Sewell et al.

(10) Patent No.: US 8,317,746 B2
(45) Date of Patent: Nov. 27, 2012

(54) AUTOMATED ALIGNMENT

(75) Inventors: Christopher M. Sewell, Sunnyvale, CA (US); Neal A. Tanner, Mountain View, CA (US); Teresa Miller, Sunnyvale, CA (US)

(73) Assignee: Hansen Medical, Inc., Mountain View, CA (US)

( * ) Notice: Subject to any disclaimer, the term of this patent is extended or adjusted under 35 U.S.C. 154(b) by 797 days.

(21) Appl. No.: 12/507,777

(22) Filed: Jul. 22, 2009

(65) Prior Publication Data

US 2010/0125285 A1  May 20, 2010

Related U.S. Application Data

(60) Provisional application No. 61/116,454, filed on Nov. 20, 2008.

(51) Int. Cl.
*A61M 31/00* (2006.01)

(52) U.S. Cl. ............. 604/95.04; 600/114; 600/146; 600/424

(58) Field of Classification Search ............ 600/101, 600/109, 114, 117, 118, 139, 146, 424; 606/130; 604/95.04, 164.12, 164.09
See application file for complete search history.

(56) References Cited

U.S. PATENT DOCUMENTS

| | | | | |
|---|---|---|---|---|
| 5,710,870 A * | 1/1998 | Ohm et al. | | 700/263 |
| 5,722,959 A * | 3/1998 | Bierman | | 604/174 |
| 5,845,646 A * | 12/1998 | Lemelson | | 128/899 |
| 6,004,271 A * | 12/1999 | Moore | | 600/445 |
| 6,061,587 A * | 5/2000 | Kucharczyk et al. | | 600/411 |
| 6,381,483 B1 * | 4/2002 | Hareyama et al. | | 600/407 |
| 6,491,701 B2 * | 12/2002 | Tierney et al. | | 606/130 |
| 6,530,913 B1 * | 3/2003 | Giba et al. | | 604/528 |
| 6,544,230 B1 * | 4/2003 | Flaherty et al. | | 604/164.12 |
| 6,551,273 B1 * | 4/2003 | Olson et al. | | 604/103.03 |
| 6,610,007 B2 * | 8/2003 | Belson et al. | | 600/146 |
| 6,669,709 B1 * | 12/2003 | Cohn et al. | | 606/167 |
| 6,905,460 B2 * | 6/2005 | Wang et al. | | 600/102 |
| 7,371,210 B2 * | 5/2008 | Brock et al. | | 600/114 |
| 7,404,824 B1 * | 7/2008 | Webler et al. | | 623/2.36 |
| 7,524,320 B2 * | 4/2009 | Tierney et al. | | 606/130 |
| 2001/0009976 A1 * | 7/2001 | Panescu et al. | | 600/424 |
| 2001/0025183 A1 * | 9/2001 | Shahidi | | 606/130 |
| 2001/0029366 A1 * | 10/2001 | Swanson et al. | | 606/29 |
| 2001/0037064 A1 * | 11/2001 | Shahidi | | 600/429 |
| 2002/0087169 A1 * | 7/2002 | Brock et al. | | 606/139 |
| 2002/0138009 A1 * | 9/2002 | Brockway et al. | | 600/485 |
| 2002/0177789 A1 * | 11/2002 | Ferry et al. | | 600/585 |
| 2003/0073908 A1 * | 4/2003 | Desai | | 600/464 |
| 2003/0074011 A1 * | 4/2003 | Gilboa et al. | | 606/130 |
| 2003/0135204 A1 * | 7/2003 | Lee et al. | | 606/1 |

(Continued)

*Primary Examiner* — Sanjay Cattungal
(74) *Attorney, Agent, or Firm* — Vista IP Law Group LLP

(57) ABSTRACT

Systems and method are disclosed whereby elongate medical instruments may be registered to adjacent tissue structures and other structures, and may be navigated and operated in a coordinated fashion to maximize ranges of motion, ease of use, and other factors. A method for registering an instrument relative to nearby structures may comprise moving a portion of the instrument between two in situ positions, tracking movement during this movement with both a kinematic model and also a localization sensor based configuration, determining the orientation of the tracked portion relative to both the instrument coordinate system used in the kinematic modeling and also a localization coordinate reference frame, and adjusting the orientation of the instrument coordinate reference frame to minimize the difference between determined orientations using the kinematic model and localization sensors. Methods and configurations for navigating coupled and registered instrument sets are also disclosed.

32 Claims, 13 Drawing Sheets

U.S. PATENT DOCUMENTS

| | | |
|---|---|---|
| 2004/0010190 A1* | 1/2004 | Shahidi .................. 600/407 |
| 2004/0176751 A1* | 9/2004 | Weitzner et al. .............. 606/1 |
| 2004/0193146 A1* | 9/2004 | Lee et al. .................... 606/1 |
| 2004/0220588 A1* | 11/2004 | Kermode et al. .......... 606/129 |
| 2005/0159789 A1* | 7/2005 | Brockway et al. ........... 607/32 |
| 2005/0182295 A1* | 8/2005 | Soper et al. ............... 600/117 |
| 2005/0182330 A1* | 8/2005 | Brockway et al. .......... 600/486 |
| 2005/0215888 A1* | 9/2005 | Grimm et al. .............. 600/426 |
| 2005/0222554 A1 | 10/2005 | Wallace |
| 2006/0095022 A1 | 5/2006 | Moll |
| 2006/0100610 A1 | 5/2006 | Wallace et al. |
| 2006/0200026 A1 | 9/2006 | Wallace |
| 2006/0271036 A1* | 11/2006 | Garabedian et al. .......... 606/41 |
| 2006/0293643 A1 | 12/2006 | Wallace et al. |
| 2007/0038181 A1* | 2/2007 | Melamud et al. ........... 604/158 |
| 2007/0043338 A1 | 2/2007 | Moll et al. |
| 2007/0060879 A1* | 3/2007 | Weitzner et al. ......... 604/95.04 |
| 2007/0156123 A1 | 7/2007 | Moll |
| 2007/0197896 A1 | 8/2007 | Moll et al. |
| 2007/0233044 A1 | 10/2007 | Wallace et al. |
| 2007/0265503 A1 | 11/2007 | Schlesinger |
| 2008/0027464 A1 | 1/2008 | Moll et al. |
| 2008/0058836 A1 | 3/2008 | Moll et al. |
| 2008/0082109 A1 | 4/2008 | Moll et al. |
| 2008/0119727 A1 | 5/2008 | Barbagli et al. |
| 2008/0140087 A1 | 6/2008 | Barbagli |
| 2008/0167750 A1 | 7/2008 | Stahler et al. |
| 2008/0262480 A1 | 10/2008 | Stahler et al. |
| 2008/0300592 A1* | 12/2008 | Weitzner et al. ............ 606/41 |
| 2009/0054884 A1* | 2/2009 | Farley et al. ................ 606/15 |
| 2009/0163929 A1* | 6/2009 | Yeung et al. .............. 606/130 |
| 2010/0125284 A1 | 5/2010 | Tanner et al. |
| 2010/0125285 A1* | 5/2010 | Sewell et al. ............. 606/130 |
| 2010/0228191 A1 | 9/2010 | Alvarez et al. |
| 2010/0331855 A1* | 12/2010 | Zhao et al. ................ 606/130 |
| 2011/0015483 A1 | 1/2011 | Barbagli et al. |

* cited by examiner

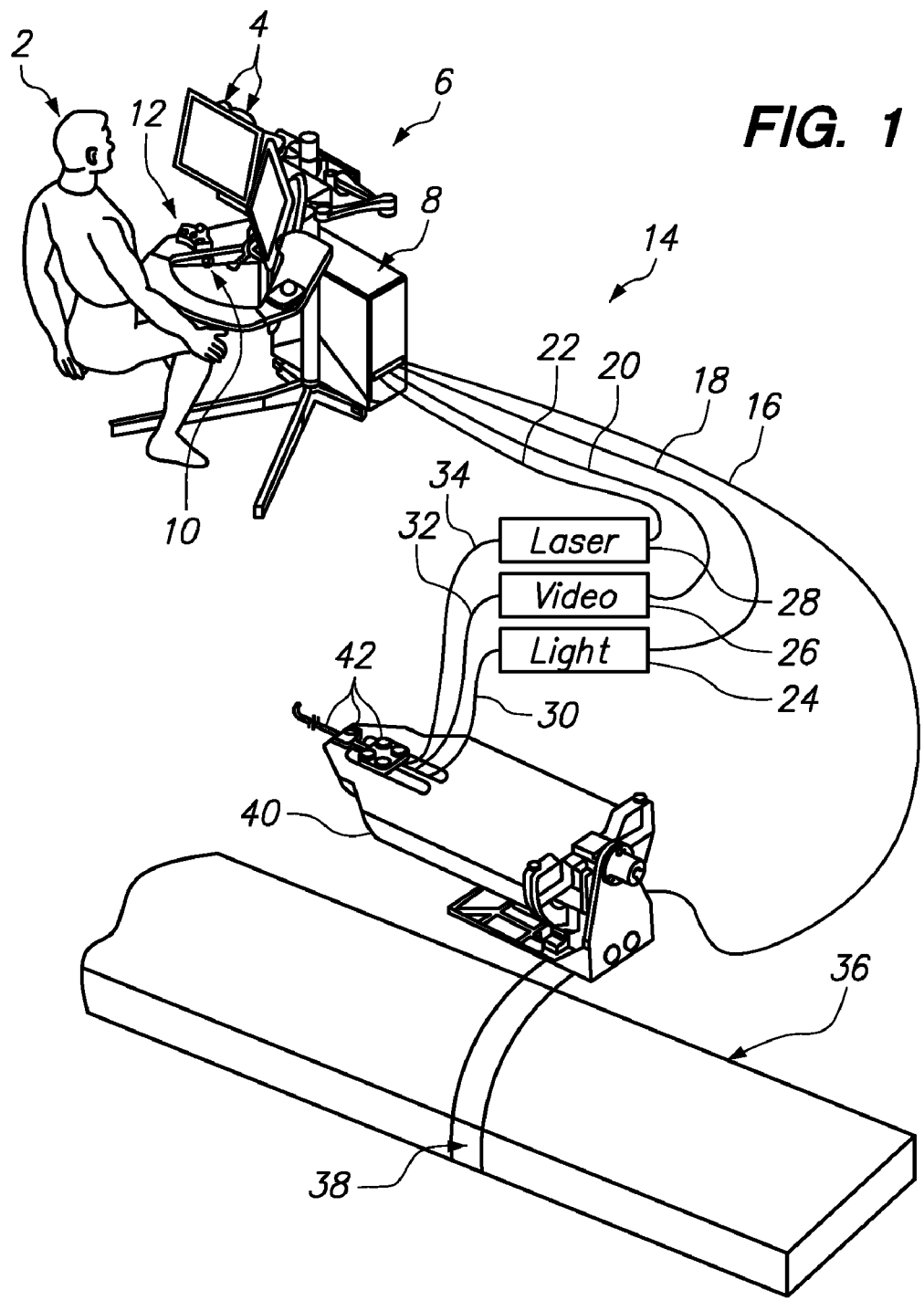

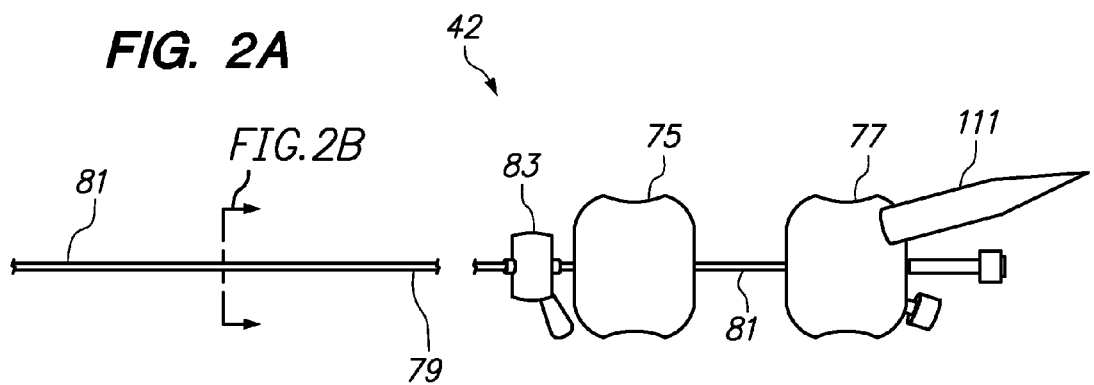
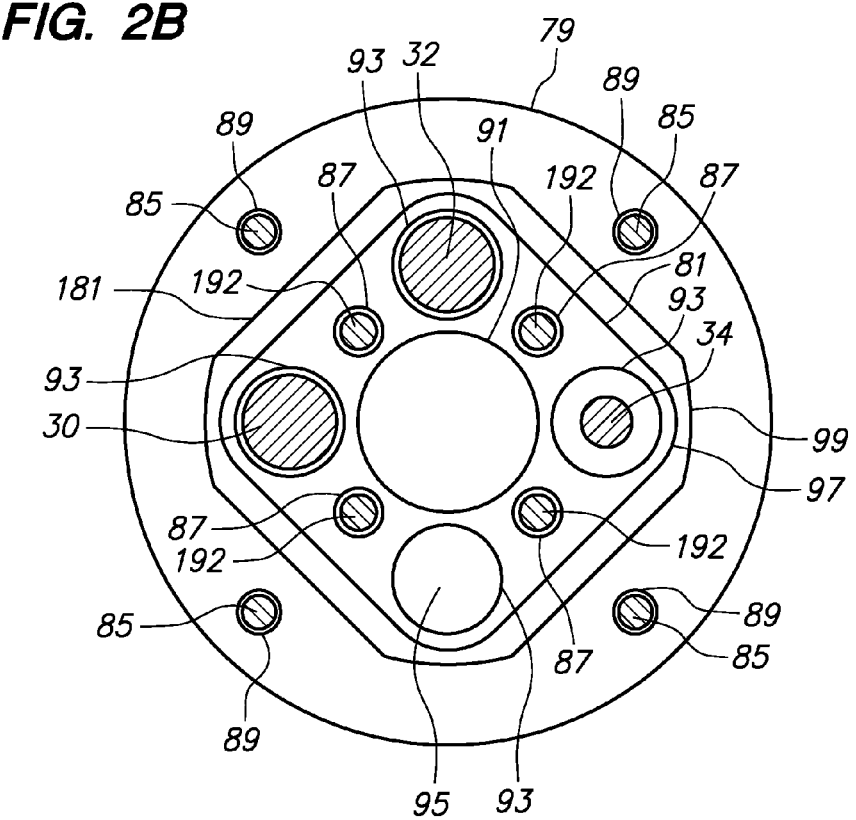

AUTOMATED ALIGNMENT

RELATED APPLICATION DATA

The present application claims the benefit under 35 U.S.C. §119 to U.S. Provisional Patent application Ser. No. 61/116,454, filed Nov. 20, 2008. The foregoing application is hereby incorporated by reference into the present application in its entirety.

FIELD OF THE INVENTION

The invention relates generally to remotely steerable medical instrument systems, such as telerobotic surgical systems, and more particularly to registration and navigation of such systems in a three-dimensional environment adjacent tissue and other structures, in furtherance of minimally invasive diagnostic and therapeutic procedures.

BACKGROUND

Minimally invasive medical techniques often rely on steerable elongate instruments, such as steerable catheters, to conduct procedures. One of the challenges in conducting diagnostic and/or interventional cases with minimally invasive instruments is understanding wherein pertinent medical instrumentation is located and/or oriented related to nearby tissue structures and other instrumentation. Imaging modalities such as radiography, fluoroscopy, and ultrasound may not be ideally suited for understanding the detailed positioning and orientation of instruments in real or near-real time. For example, it is possible to use multiple planes and/or imaging field of view perspectives with modalities such as fluoroscopy to determine the location and orientation of instrumentation that shows up in the images relative to anatomy which also is featured in the images—but multiplanar imaging may not be convenient or accurate enough to facilitate realtime navigation of minimally invasive instruments through various anatomical spaces. Further, it is possible to utilize kinematic models of instruments to understand the positions and orientations of portions of such instruments, but compliance, control mechanism slack, repositioning, and other factors may lead to the desire to recalibrate kinematic-based position and/or orientation models relative to the actual anatomy from time to time. Embodiments are presented herein to address these and other challenges.

SUMMARY

One embodiment is directed to a method for registering an elongate medical instrument relative to nearby anatomical structures, comprising moving a portion of an elongate medical instrument between a first position in situ and a second position in situ relative to an instrument coordinate reference frame; tracking movement of the portion relative to the instrument coordinate reference frame using a kinematic model, and also tracking movement of the portion relative to a localization coordinate reference frame using one or more localization sensors coupled to the portion; determining the orientation of the portion relative to both the instrument coordinate reference frame and the localization coordinate reference frame; and adjusting the orientation of the instrument coordinate reference frame to minimize the difference between determined orientations using the kinematic model and localization sensors. The first position in situ may be a substantially straight position for the portion of the elongate instrument. In the first position in situ, the portion may be substantially coincident with a coordinate axis representing a substantially unloaded, substantially straight, longitudinal axis of the portion of the elongate instrument. The portion may be a distal portion of the elongate instrument. The elongate medical instrument may be coaxially positioned through a working lumen of a sheath instrument, with the distal portion retracted toward the working lumen of the sheath instrument with the sheath instrument in a substantially straight position in the first position in situ. The elongate medical instrument may be a robotic catheter. The first position in situ may be achieved with an electromechanical autoretraction command. Tracking movement of the portion relative to the instrument coordinate reference frame using a kinematic model may comprise determining an estimated position of the portion based at least in part upon an insertion position of the portion and positions of one or more steering positioners comprising the elongate medical instrument. In one embodiment, the elongate medical instrument may be a steerable catheter, and the one or more steering positioners may comprise steering pullwires. The one or more localization sensors may be potential difference based localization sensors; in another embodiment they may be magnetic field based localization sensors. In one embodiment, the second position in situ may be a curved position for the portion of the elongate instrument. The curved position may have a minimum radius of curvature, and a user interface may be configured to assist an operator in positioning the portion of the elongate instrument into a curved position having a radius of curvature greater than or equal to the minimum radius of curvature. The user interface may be configured to present the operator with a cylindrical shaped guiding envelope past which the elongate instrument portion should be driven to place the portion into a curved position having a radius of curvature greater than or equal to the minimum radius of curvature. In one embodiment, determining the orientation of the portion relative to the localization coordinate reference frame may comprise selecting a subset of available localization data collected for movement of the portion between the first position in situ and the second position in situ, fitting a line through the subset, and determining orientation relative to the localization coordinate reference frame based upon the position of the line. Selecting a subset of available localization data may comprise fitting a line through an initial subset of available localization data collected for movement of the portion between the first position in situ and the second position in situ, the initial subset being one that is presumed to contain data that is less likely to be noisy. A method may further comprise sequentially adding additional data from the available localization data collected to form an updated subset of data; fitting a line through the updated subset of data; determining the quality of fit of the line through the updated subset of data; and determining, based upon the quality of fit, an optimized subset of data for determining the orientation of the portion relative to the localization coordinate reference frame. Determining the quality of fit may comprise determining the root mean square error of data comprising the updated subset of data relative to the line fitted through such data. Moving a portion of an elongate medical instrument between a first position in situ and a second position in situ may be conducted as an overlay to other concurrent navigation of the elongate medical instrument. In one embodiment, the method may further comprise stopping other navigation of the elongate medical instrument before initiating the moving of a portion of an elongate medical instrument between a first position in situ and a second position in situ. In one embodiment, an IVUS imaging assembly may be coupled to the elongate medical device, and tracking movement may further comprise observing images produced by the IVUS imaging assembly. A method may further comprise allowing for an operator adjustment of the orientation of the instrument coordinate reference frame, and synchronizing adjustment of an associated master input device coordinate reference frame to retain instinctiveness of the master input device relative to observed operation of the elongate medical device.

Another embodiment is directed to a system for registering an elongate medical instrument relative to nearby anatomical structures, comprising a remotely navigated working elongate medical instrument having a distal end, an elongate body, and one or more localization sensors coupled to the elongate body; a remotely navigated secondary instrument having a working lumen configured to slidably engage the elongate medical instrument; a localization system coupled to the one or more localization sensors and configured to determine the positions of such sensors relative to a localization coordinate reference frame; a processor operatively coupled to the working elongate medical instrument and secondary instrument, and configured to determine the position thereof relative to an instrument coordinate reference frame based upon kinematic models for the instruments; wherein the processor is configured to move a portion of the working elongate medical instrument between a first position in situ and a second position in situ relative to the instrument coordinate reference frame; track movement of the portion relative to the instrument coordinate reference frame using a kinematic model, and also tracking movement of the portion relative to a localization coordinate reference frame using one or more localization sensors coupled to the portion; determine the orientation of the portion relative to both the instrument coordinate reference frame and the localization coordinate reference frame; and adjust the orientation of the instrument coordinate reference frame to minimize the difference between determined orientations using the kinematic model and localization sensors. The working elongate medical instrument may be a flexible catheter. The secondary instrument may be a flexible sheath catheter. The flexible catheter may be a robotically steerable catheter, wherein the processor may be configured to move the catheter between a first position and a second position electromechanically. The processor may be configured to track movement of the portion using a kinematic model by determining an estimated position of the portion based at least in part upon an insertion position of the portion and positions of one or more steering positioners comprising the elongate medical instrument. The one or more steering positioners may comprise steering pullwires. The one or more localization sensors may be potential difference based localization sensors. The one or more localization sensors may also be magnetic field based localization sensors. The first position may be a substantially straight position, and the second position may be a curved position wherein the portion has a radius of curvature greater than or equal to a threshold minimum radius of curvature. The processor may be configured to assist an operator in positioning the portion into the curved position. The processor may direct a user interface to present to the operator a cylindrincal shaped guiding envelope past which the elongate instrument portion should be driven to place the portion into a curved position having a radius of curvature greater than or equal to the minimum radius of curvature. The processor may be configured to autoretract the catheter between a first position and a second position electromechanically.

BRIEF DESCRIPTION OF THE DRAWINGS

FIG. 1 illustrates one embodiment of a robotic catheter system.

FIGS. 2A-2C illustrate aspects of one embodiment of a robotic catheter instrument set.

DETAILED DESCRIPTION

Figure 2C:
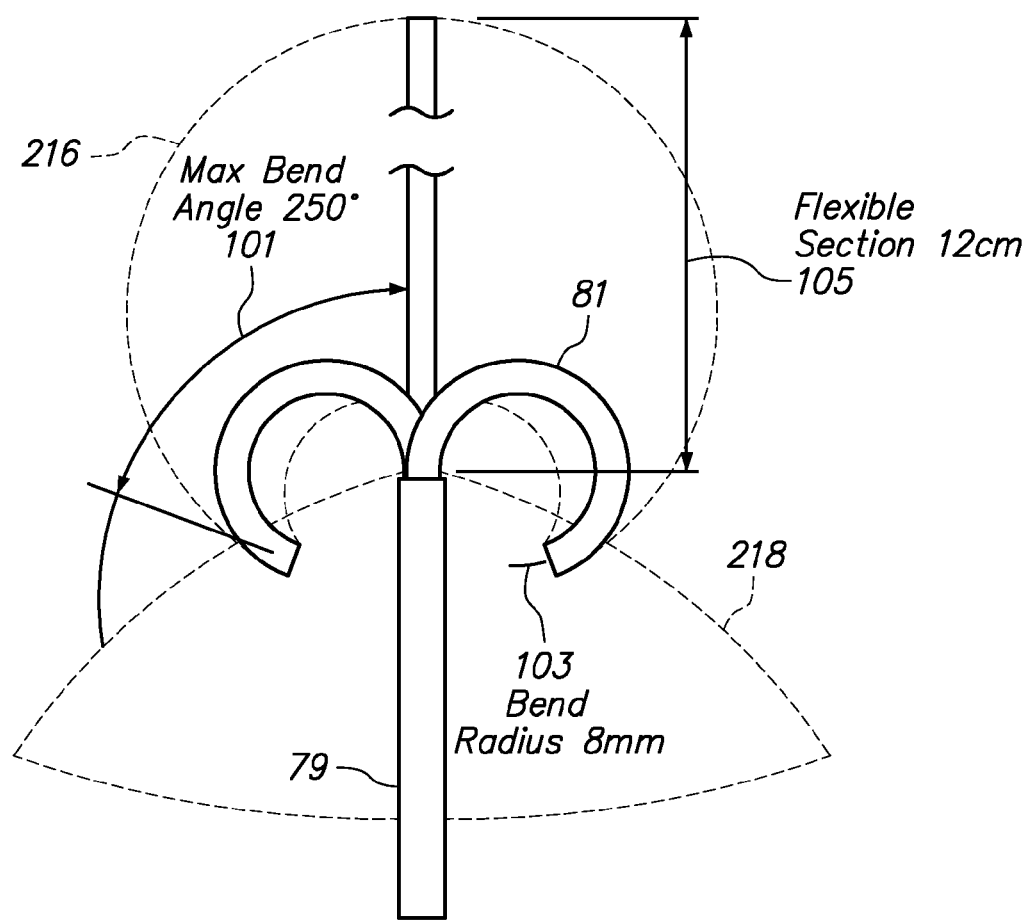

Referring to FIG. 1, a system (14) is depicted wherein an operator (2) is seated at an operator workstation (6) in a position such that he has access to one or more displays (4), in addition to one or more input devices, such as a master input device (10) and an operator button console or pendant (12). A computing system or controller (8) comprising a processor is operably coupled via a cable (16) to a robotic instrument driver (40), which is coupled to an operating table (36) with a fixed mounting member (38). Similar systems have been described, for example, in U.S. patent application Ser. Nos. 11/073,363; 11/179,007; 11/176,598; 11/176,957; 11/481, 433; 11/331,576; 11/637,951; 11/640,099; 11/678,001; 11/690,116; 11/804,585; 11/829,076; 11/833,969; 11/852, 255; 11/906,746; 11/972,581; 12/032,626; 12/398,763; and 12/504,564, each of which is incorporated by reference in its entirety into this patent application. It is important to note that while certain aspects of the embodiments described herein are specifically applicable to electromechanically navigated medical instrument systems, other aspects, such as the registration aspects described below, are broadly applicable to steerable or navigable medical instruments which may or may not comprise electromechanical drive systems, and such variations are within the intended scope of this invention.

Referring again to FIG. 1, the computing system in the depicted exemplary system is operably coupled to a laser therapy system (28), a video system (26), and a lighting system (24) configured to provide endoscopic lighting for the video system (26) by respective cables (22, 20, 18) connecting such systems to the computing system (8). The computing system, via such couplings, is configured to control lighting, video image capture, and laser energy emission, preferably in response to commands input by the operator (2) to interfaces such as the pendant (12) or master input device (10) at the operator workstation (6). Other input devices, such as a foot pedal (not shown), may also be operably coupled to the computing system (8) to enable an operator (2) to execute commands, such as video capture, laser energy emission, and/or lighting, via such input. The laser system (28) is operably coupled to the depicted robotic instrument assembly (42) via a laser energy transmission fiber assembly, or "laser fiber", (34) while the video system (26) is operably coupled to the instrument assembly (42) via an optics bundle (32) comprising a plurality of optical transmission fibers. The lighting system (24) is similarly operably coupled to the robotic instrument assembly (42) via a light transmission bundle (30) preferably comprising optical transmission fibers. Such a system may be broadly applied to various clinical and diagnostic scenarios pertinent to healthcare, including but not limited to interventions and diagnostics within the bloodstream, such as minimally invasive, endocardial cardiac ablation, valve repair, and other procedures.

Referring to FIGS. 2A-2C, aspects of the depicted elongate steerable instrument assembly (42) are described, such assembly being configured for endoscopic diagnosis and/or intervention in an environment wherein direct optical visualization (for example, with an optical image capture device such as a fiberscope or camera chip) is desired, such as with kidney stone interventions using trans-urethral endolumenal access.

Referring to FIG. 2A, an instrument assembly (42) is depicted comprising an inner elongate member, or "guide member", (81) proximally coupled to a specialized inner instrument base housing (77) which is removably coupleable to an image capture device member (111) preferably comprising a camera chip (not shown). The midsection and distal portion of the inner elongate member (81) are shown slidably coupled and inserted through a working lumen defined through an outer elongate member, or "sheath member", (79). Also depicted are the outer instrument base housing (75) and a clamp (83) configured to assist with coupling to aspects of an instrument driver (40—such as that shown in FIG. 1). FIG. 2B is a cross sectional view of the instrument assembly (42) depicted in FIG. 2A. Referring to FIG. 2B, the inner elongate member (81) is threaded through a working lumen (181) defined by the outer elongate member (79). The geometric interaction of the outer elongate member working lumen (181), having a substantially square cross sectional shape with rounded corner surfaces (99), and the outer shape of the inner elongate member (81), which in the depicted embodiment has a square cross sectional outer shape with rounded corners (97), is designed to allow for slidable coupling of the two elongate members (for example, to allow insertion of one relative to the other without a great degree of load applied), while also preventing relative rolling, or rotation, of the two elongate members relative to each other—at least in the areas where they are coupled.

Referring again to FIG. 2B, a relatively complex embodiment is shown for illustrative purposes, wherein the outer elongate instrument member (79) defines four lumens (89) for four control elements (85), such as metallic, semi-metallic, polymeric, or natural pull or pushwires, to enable relatively sophisticated steering of the outer elongate instrument member (79), when such control elements (85) are coupled to a distal portion of the outer elongate instrument member (79), and also coupled to actuator motors within an instrument driver (40) via a mechanical interfacing with rotatable members coupled to the outer instrument base housing (75), as described in the aforementioned incorporated by reference applications. In other words, in one embodiment, the outer instrument may comprise a 4-wire electromechanically steerable sheath instrument capable of omnidirectional steering (for example, when three or four wires terminate at the same position distally), and capable of more complex shapes when one or more wires terminate more proximally than others. Preferably each wire is actuated utilizing an independently operable motor assembly in the instrument driver (40). In other embodiments, such as the embodiments described in the aforementioned incorporated by reference applications, the outer instrument may be much more simple—for example, with only one, two, or even zero control elements. The outer (79) and inner (81) elongate instrument members may comprise polymeric coextrusions.

Referring again to FIG. 2B, the depicted embodiment of the inner elongate instrument member is also relatively sophisticated, defining four instrumentation lumens (93) and a central, larger diameter, working lumen (91) preferably substantially aligned with the longitudinal axis of the inner elongate member (81) and sized to accommodate desired working tools, such as a mini-grasper tool, such as those available from suppliers such as Novare, Inc., or a collapsible basket tool, such as those available from suppliers such as Boston Scientific, Inc. Like the depicted embodiment of the outer elongate instrument member (79), the inner elongate instrument member (81) comprises four control elements (192), such as pushwires and/or pullwires made from metallic, semimetallic, polymeric, or natural materials, threaded through four control element lumens (87). As described above in reference to the outer elongate member (79), this embodiment may be omnidirectionally steerable and/or capable of complex curvatures, via operable coupling of such control elements (191) between distal portions of the inner elongate member (81) and actuation motors within an instrument driver (40). In other embodiments, a simpler configuration comprising one, two, or three control elements (192) may be desired.

Referring again to FIG. 2B, the four instrumentation lumens (93) defined within the depicted embodiment of the inner elongate instrument member (81) are configured to accommodate relatively fixed (in other words, the lumens are large enough to accommodate assembly of the instrument, but small enough to provide a relatively close fit thereafter to prevent significant relative motion) positioning of a light bundle (30) and video/optics bundle (32). Another instrumentation lumen (93) is more loosely and slidably coupled to a laser fiber (34), to allow for relative insertion, retraction, and sometimes roll (depending upon the curvature of the overall assembly) intraoperatively. The fourth instrumentation lumen (93) may be utilized as a saline or other fluid (for example, a contrast agent or medicinal fluid) infusion or flush channel (95) for intraoperative use. Referring to FIG. 2C, in one embodiment, it is desirable that about twelve centimeters of a more flexible, steerable distal portion (105) of the inner elongate instrument member (81) be able to protrude out the distal end of the outer elongate instrument member (79), and that the inner elongate instrument member (81) be capable with such protrusion of forming a bend radius (103) of approximately eight millimeters, with a maximum bend angle (101) of approximately 250 degrees.

The system described above in reference to FIGS. 1-2C is very sophisticated and capable, but if it is not registered or aligned to pertinent coordinate systems, such as the world coordinate system to which other structures, such as other instruments and tissue structures and maps thereof, may be registered, its utility in medical intervention may not be fully realized. FIGS. 3A-3I illustrate a novel technique for addressing this registration/alignment challenge.

Figure 3A:
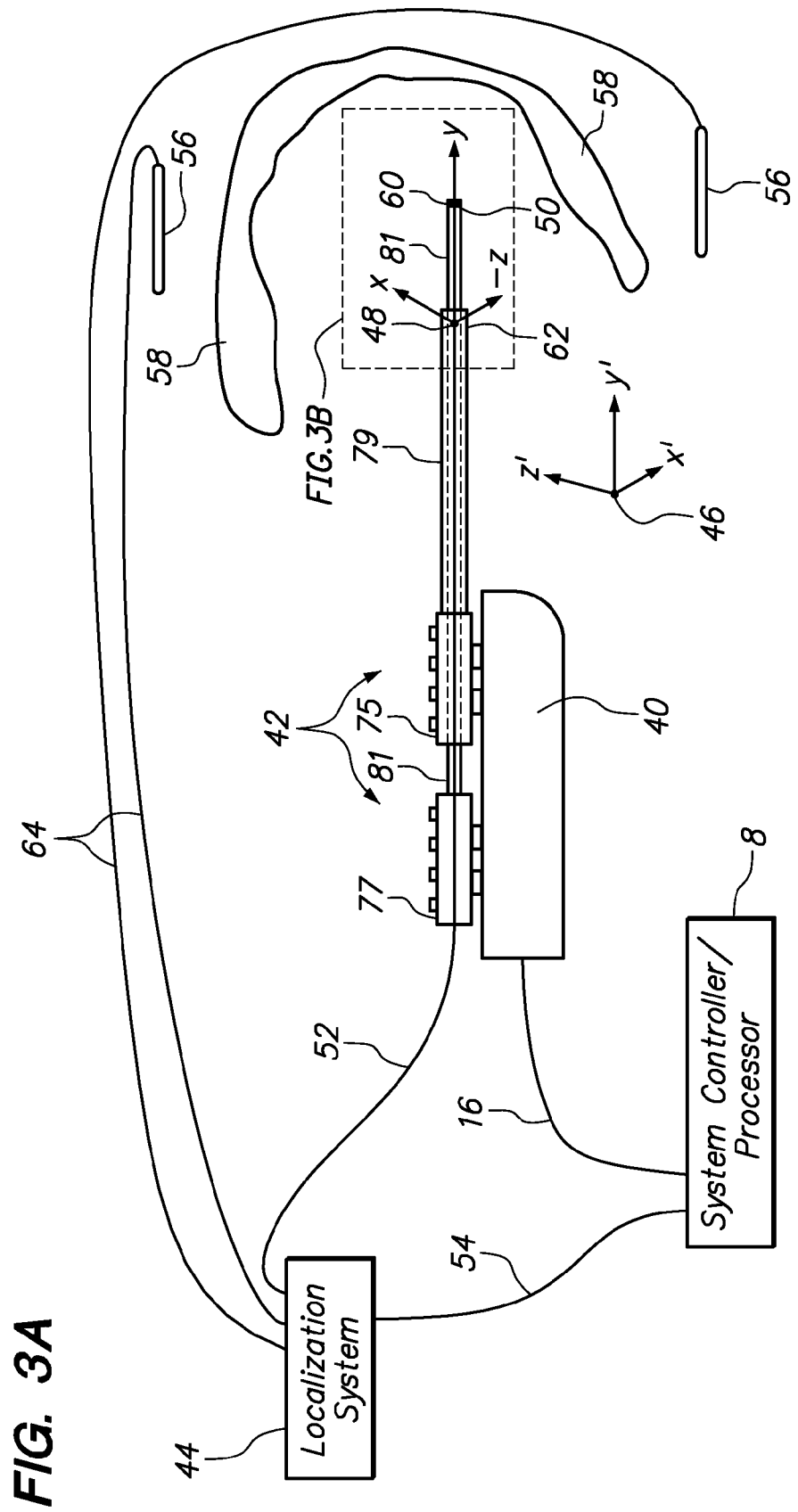
FIGS. 3A-3I illustrate embodiments of a registration or alignment technique in accordance with the present invention.

Referring to FIG. 3A, a more simplified system is depicted, comprising an outer steerable instrument (79) coaxially and operably coupled with an inner steerable instrument (81), the two again comprising an instrument assembly (42) which is drivably coupled to an electromechanical instrument driver (40) which is operatively coupled, via an electronic communication link (16) such as a cable, to a system controller (8) comprising a processor. The instruments may comprise catheters, probes, or other elongate minimally invasive instruments. In the depicted embodiment, the inner steerable instrument distal tip (60) is coupled to one or more localization sensors (50) operatively coupled, via an electronic communication link (52) such as a small cable, to a localization system (44). The localization system (44) preferably is configured to determine, observe, or track the spatial coordinates of the one or more sensors (50) relative to a localization coordinate reference frame (46—the xprime/yprime/zprime coordinate reference frame) that preferably is a substantially absolute coordinate reference frame, in that it is preferably coupled to something relatively immovable relative to the world coordinate system (i.e., of the floor of the operating room), such as a heavy operating table. The localization system may comprise a potential difference based system, such as those available under the tradename EnSite® from St. Jude Medical, Inc. of St Paul, Minn.; alternatively the localization system may be ultrasound based, such as the RPM® system from Boston Scientific Corporation, electromagnetic flux based, such as the systems available from the Biosense Webster division of Johnson & Johnson, Inc., or Bragg-fiber based, such as the systems available from Luna Innovations, Inc. The depicted localization system (44) is a potential difference based system, and operates by monitoring electrical potential differences between one or more localization sensors (50) coupled to an instrument portion, and two or more conductive skin patches (56), also connected to the system (44) by electronic communication links (64) such as a small cables. Such a system is configured to provide positional information regarding the one or more sensors (50) in real or near-real time, but generally is not configured to provide roll orientation information. In other words, twisting of the instrument about its longitudinal axis may very well go undetected by such a system. The depicted instrument assembly (42) does not have a localization sensor coupled to the outer elongate instrument (79), but the position of the distal end (62) of the outer elongate instrument may be inferred through its relationship with the distal end (60) of the inner instrument, which has at least one localization sensor (50) coupled to it. Indeed, in one embodiment, at least two localization sensors are coupled longitudinally in sequence to the inner instrument (81), such as by a known distance roughly equivalent to the amount of inner instrument portion which may be extended or inserted beyond the distal tip (62) of the outer instrument (79), or in other embodiments approximately half or approximately one quarter of this distance, to enable the localization system and/or the control system to determine not only the position of the distal portion of the inner instrument (81), but also the spatial position/orientation of the longitudinal, or Y, axis of the instrument coordinate reference frame (48). In other words, with two localization sensors, position information regarding each, and a known distance between each of the sensors and the instrument coordinate reference frame (48), the position of the instrument coordinate reference frame (48) and orientation of the Y axis thereof may be determined. In another embodiment, rather than having two localization sensors to characterize the system in this way, a single 5 degree of freedom sensor (providing position and also orientation information) may be utilized, given the distance between such sensor and the instrument coordinate reference frame, and an assumption regarding a known shape of the instrument body in between, such as a substantially straight position or shape. For convenience, the illustrations of FIGS. 3A-3E feature one localization sensor (50), which may be, for example, a single 5 degree of freedom localization sensor, or may be thought of as representing a series of two position-only localization sensors. Further, the locations of both instruments may be determined utilizing established kinematic relationships and some basic assumptions regarding lack of contact with outside forces, as described in the aforementioned incorporated by reference applications. As described briefly above, one of the challenges to accurate navigation relative to nearby tissue structures and other instruments is registering one or more coordinate systems pertinent to the operation of the instruments relative to other known coordinate systems, such as those of other tissue structures, or more absolute coordinate systems, such as that of the world, or that of a relatively stable and well-physically-grounded localization system. With a system such as that depicted in FIG. 3A, localization sensing and trajectory comparison may be utilized to accomplish such registration, as described in reference to FIGS. 3B-3I.

Figure 3B:
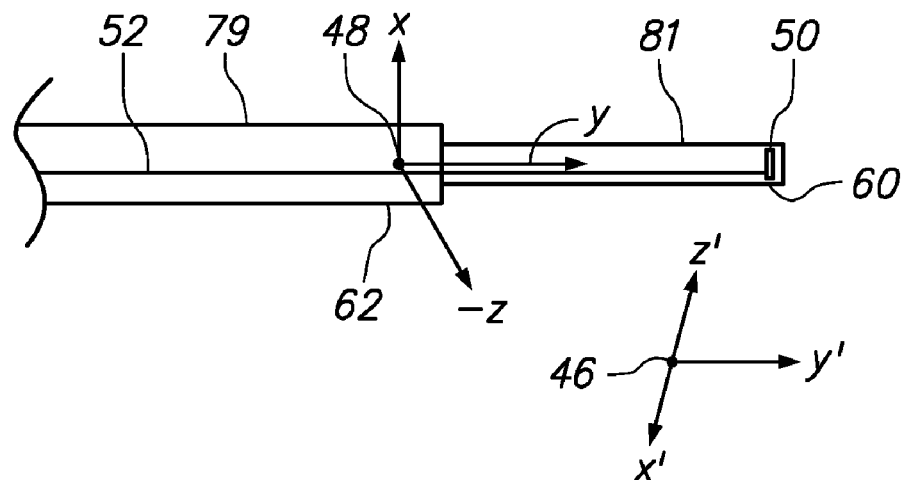
Figure 3C:
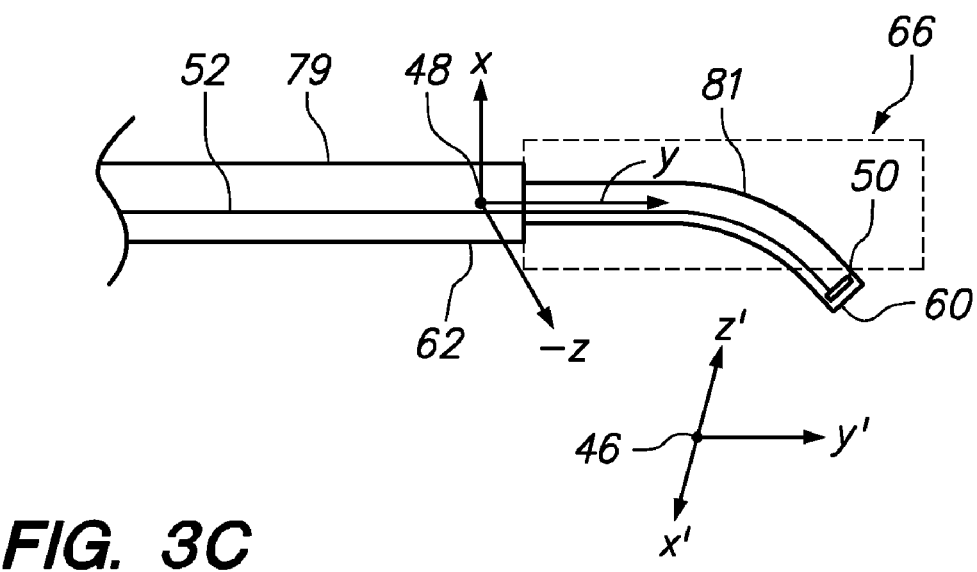
Figure 3D:
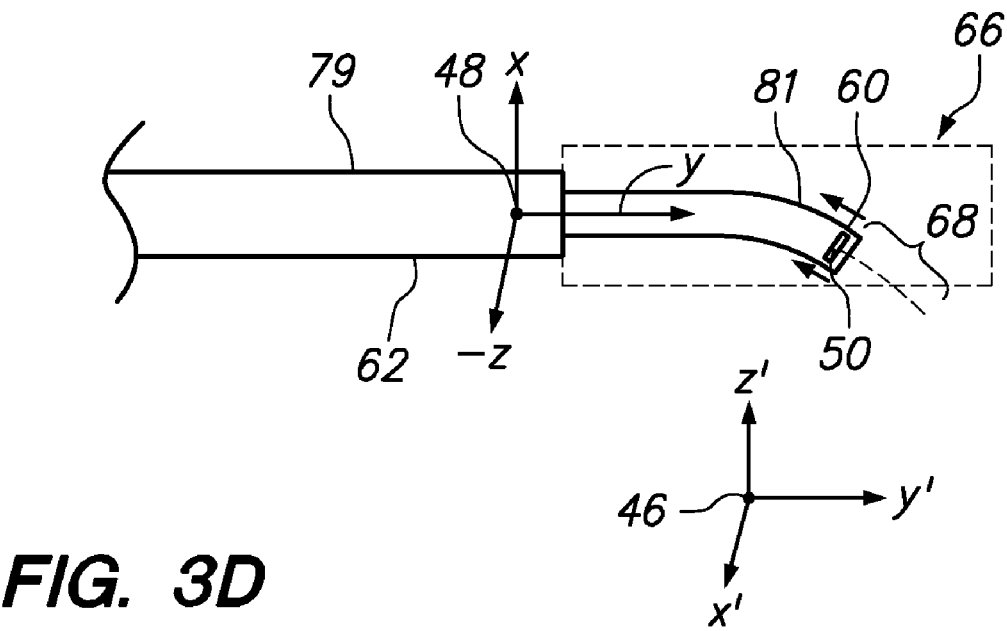
Figure 3E:
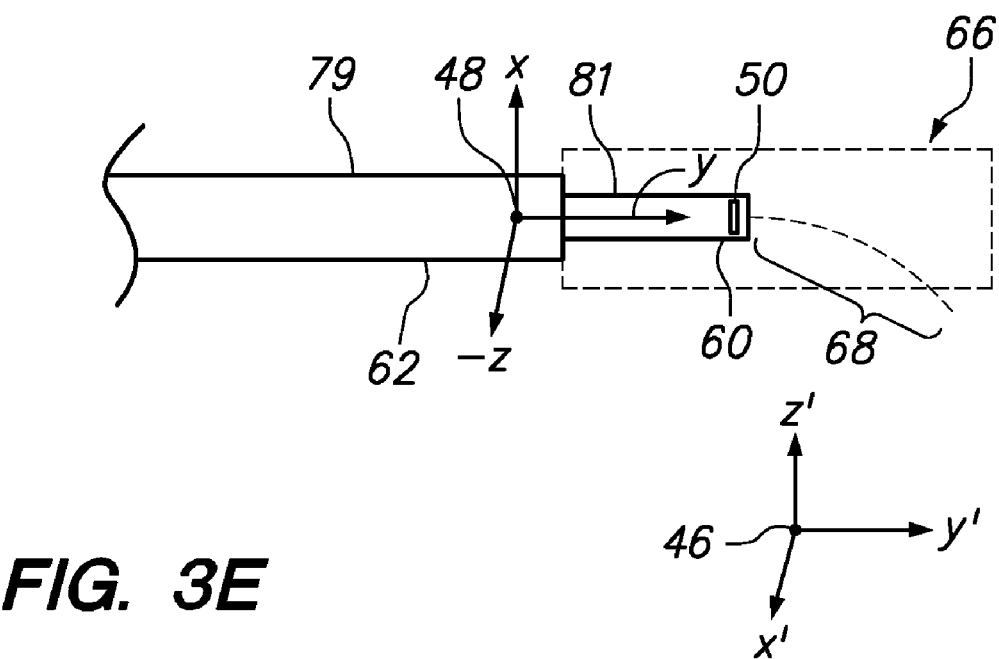

Referring to FIG. 3B, a close up view of the distal portions of the instruments depicted in FIG. 3A are illustrated. At the outset, the instruments (79, 81) are operated using a kinematic-based control paradigm wherein kinematic formulas associated with movement of mechanisms within the instrument driver (element 40 in FIG. 3A) that are coupled to the instrument assembly (42) may be utilized to infer where in space the distal portions (62, 60) of the instruments (79, 81) are in space relative to an instrument coordinate reference frame (48, X/Y/-Z as depicted) positioned at the distal tip (62) of the outer instrument (79), which has no localization sensor. When the inner instrument (81) is moved, its position may be determined with the localization sensor (50) and system, and also with the kinematic based configuration. In one embodiment, it is desirable to navigate the inner instrument (79) to a curved position, such as that depicted in FIG. 3C, which has enough curvature and insertion length to lie outside of a pre-prescribed sampling zone boundary, which may be displayed to an operator as a semitransparent cylindrical shape in a three dimensional virtual navigation environment, such as that described in the aforementioned incorporated by reference applications, to assist the operator in achieving such curvature. Referring to FIG. 3D, subsequent to achieving the curved position depicted in FIG. 3C, the inner instrument (81) may be retracted along the path it occupied as it was inserted into the curved position, a scenario which may be termed "autoretract" when electromechanically accomplished in accordance with the incorporated by reference applications. As the inner instrument (81) is retracted, or autoretracted, a series of datapoints (68) may be collected using two position tracking schemas: the kinematics based approach relative to the instrument coordinate reference frame (48), and the localization based approach relative to the localization coordinate reference frame (46). Referring to FIG. 3E, the retracting or autoretracting may be stopped when the inner instrument (81) is in a straight position, substantially aligned with the longitudinal (or "Y") axis of the outer instrument (79), and protruding a predetermined distance, such as between 8 and 20 millimeters, from the distal tip (62) of the outer instrument (79).

Figure 3F:
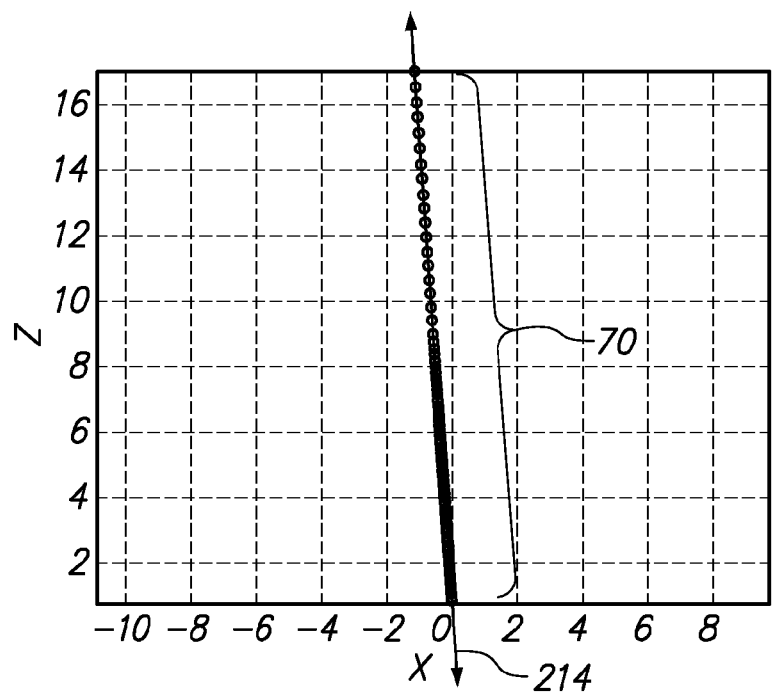

In another embodiment, the exact opposite pattern may be conducted, with the inner instrument (81) starting in a curved position, then retracted, or "autoretracted" back toward the outer instrument (79) distal tip (62). This order of events may be advantageous because retraction is generally a safe, non-interfering maneuver relative to other surrounding structures, such as tissue structures, and also because particularly with "autoretract" functionality, the trajectory generally is a straight line when projected in the XZ plane, as illustrated in FIG. 3F. In another embodiment, a retraction or autoretraction, followed by a nearly arbitrary manually navigated path (so long as such path is on some kind of curve that is not straight along the axis of the instrument), may be utilized to find all three orientation degrees of freedom, or used to just find the roll offset after an axial pointing direction is determined using two sequentially-longitudinally positioned localization sensors, or a single 5 degree of freedom localization/orientation sensor.

Referring to FIG. 3F, a sample set of data (70) acquired during autoretraction of an inner instrument relative to an instrument coordinate reference frame and determined using the kinematics based approach is depicted (positions projected in the XZ plane), with a best fit line (214) fitted through it. Since autoretraction, by definition, is defined as electromechanically retracting straight back to the outer instrument (79) along the path previously occupied during insertion, the kinematic approach predictably has a very clean dataplot with little fit error (such as root mean square, or "RMS" error) between the fitted line (214) and the data.

Figure 3G:
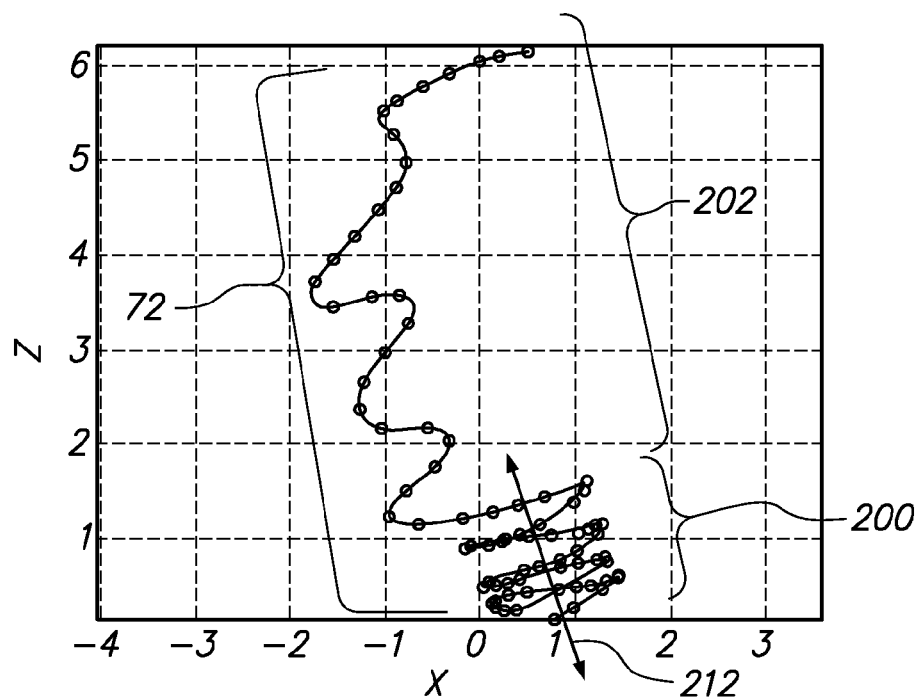
Figure 3H:
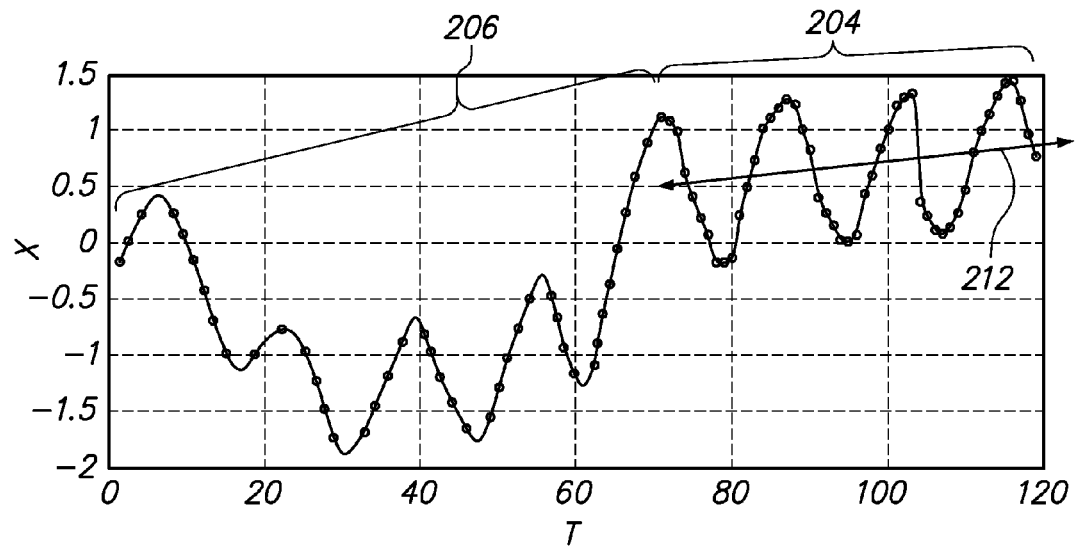
Figure 3I:
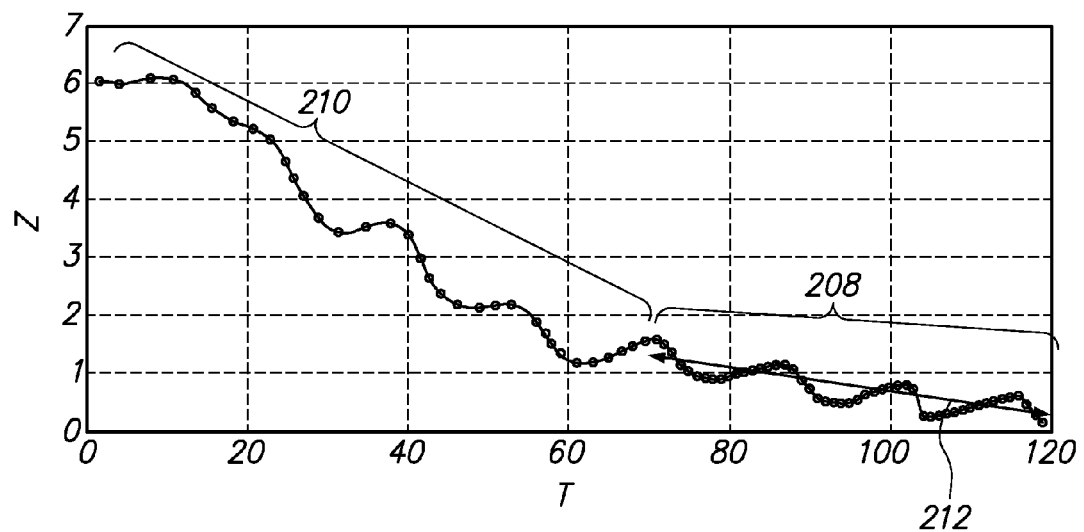

Referring to FIG. 3G, a sample set of data (72) acquired during the same autoretraction is depicted (positions projected in the XZ plane) for comparison, the plot in FIG. 3G being based upon the localization data and relative to the localization coordinate reference frame. As one can see, the localization data is relatively noisy. This noise may be based upon nonlinearities built into the software code resident on the localization system, data artifacts associated with breathing of the patient, physical interference between the subject instrument set and other nearby structures, and other reasons. Rather than simply fitting a line through all of the data and having a fitted line with a relatively large error, such as RMS error, it is preferred to sequentially address the data, starting with the data most likely to not be representative of a scenario wherein aspects of the instrument set are in physical contact with other structures: the data closest to full retraction or autoretraction. It is also preferable, however, to base the fitted line on more rather than less data. In one embodiment, as a compromise, line fitting and fitting quality analysis are conducted for a series of "data windows". The first window fitted and analyzed is a series of points closest to retraction. Subsequently, one or more additional points are added to the data window, points which are immediately adjacent the previous data window, and a new line is fitted for the new data window and fit quality analysis (such as RMS error calculation) is conducted. The data window is enlarged until the quality of fit increases past a predetermined threshold. In this embodiment, the largest data window having an acceptable fit is considered the "included data" (200) and the line fit therethrough (212) is deemed representative of the localization data for the subject retraction. The remaining data is considered "excluded data" (202). In one embodiment, to ensure that a line perpendicular (not shown) to the selected line (212) through the included data (200) is not selected, the same localization data is plotted broken down in determined X positions versus time (FIG. 3H) and determined Z positions versus the same time scale (FIG. 3I), and a similar data windowing schema is utilized to plot lines through included X data (204), as opposed to excluded X data (206), and included Z data (208), as opposed to excluded Z data (210), separately. This additional step of fitting X and Z separately, each as a function of time, preserves time dependent directionality of the data.

In one very simplified embodiment, alignment could be conducted based on a much smaller set of data—such as two data points: one data point from a fully retracted inner instrument position, and one data point from an extended and curved inner instrument configuration. This embodiment would, of course, be more prone to inaccuracy due to noise in such a small dataset.

Figure 4:
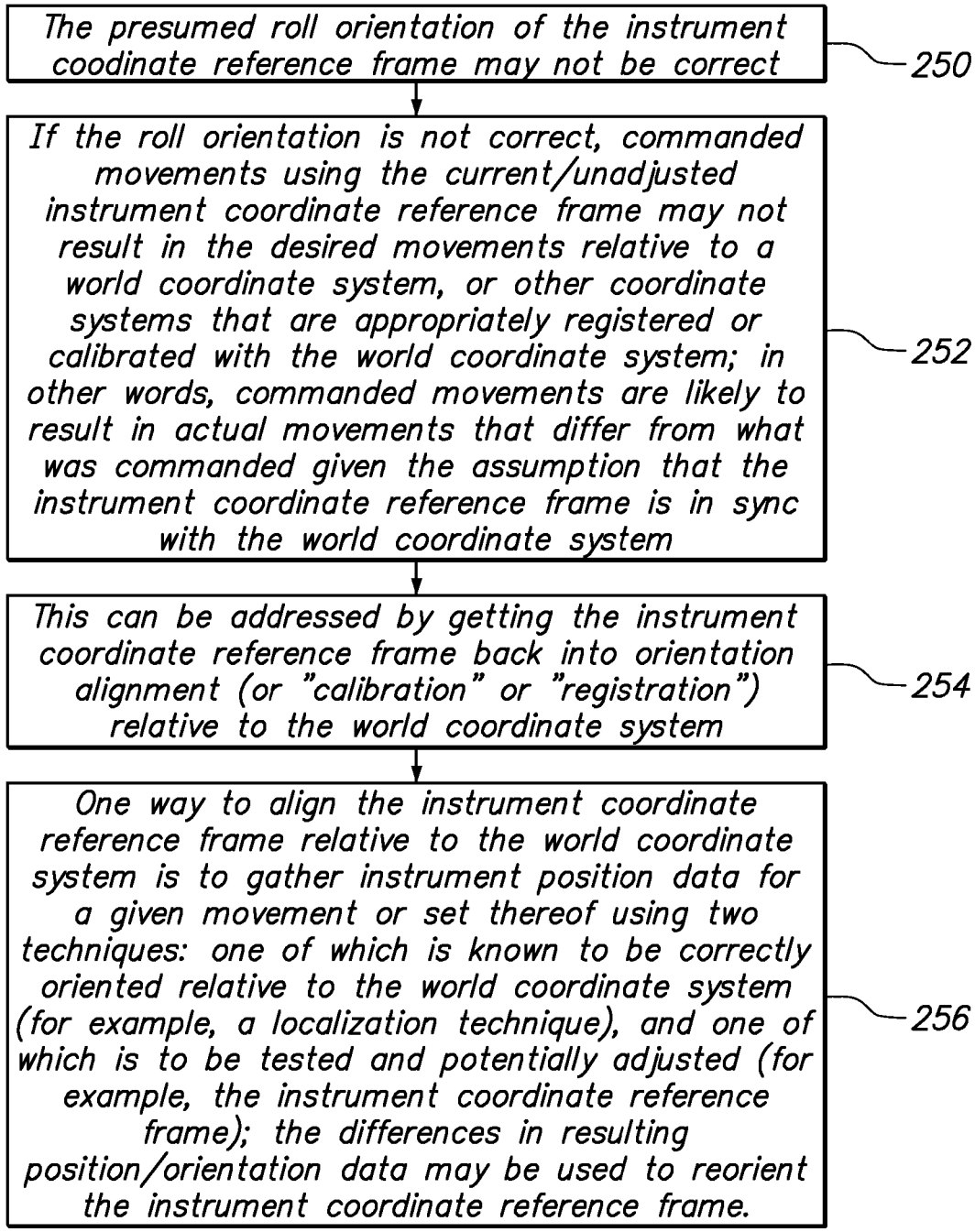
FIG. 4 illustrates one embodiment of a registration or alignment technique in accordance with the present invention.
Figure 5:
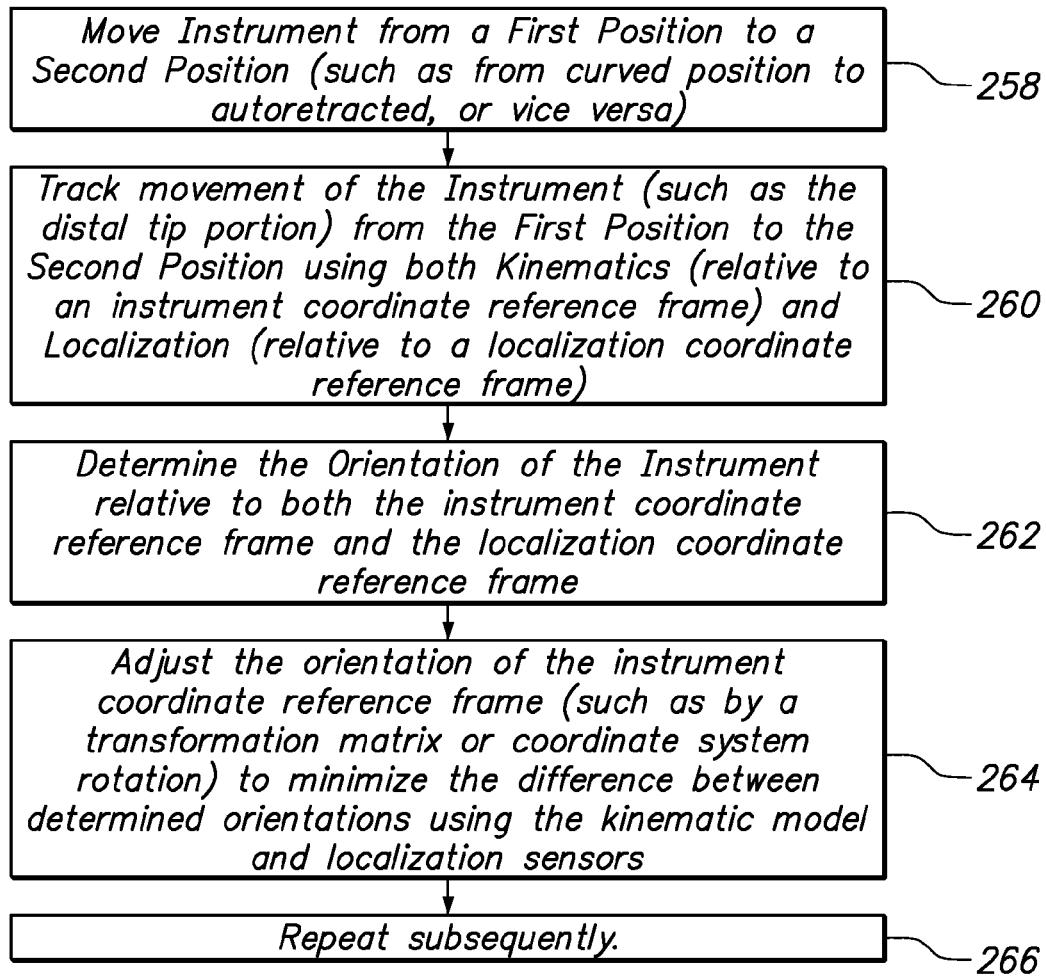
FIG. 5 illustrates one embodiment of a registration or alignment technique in accordance with the present invention.
Figure 6:
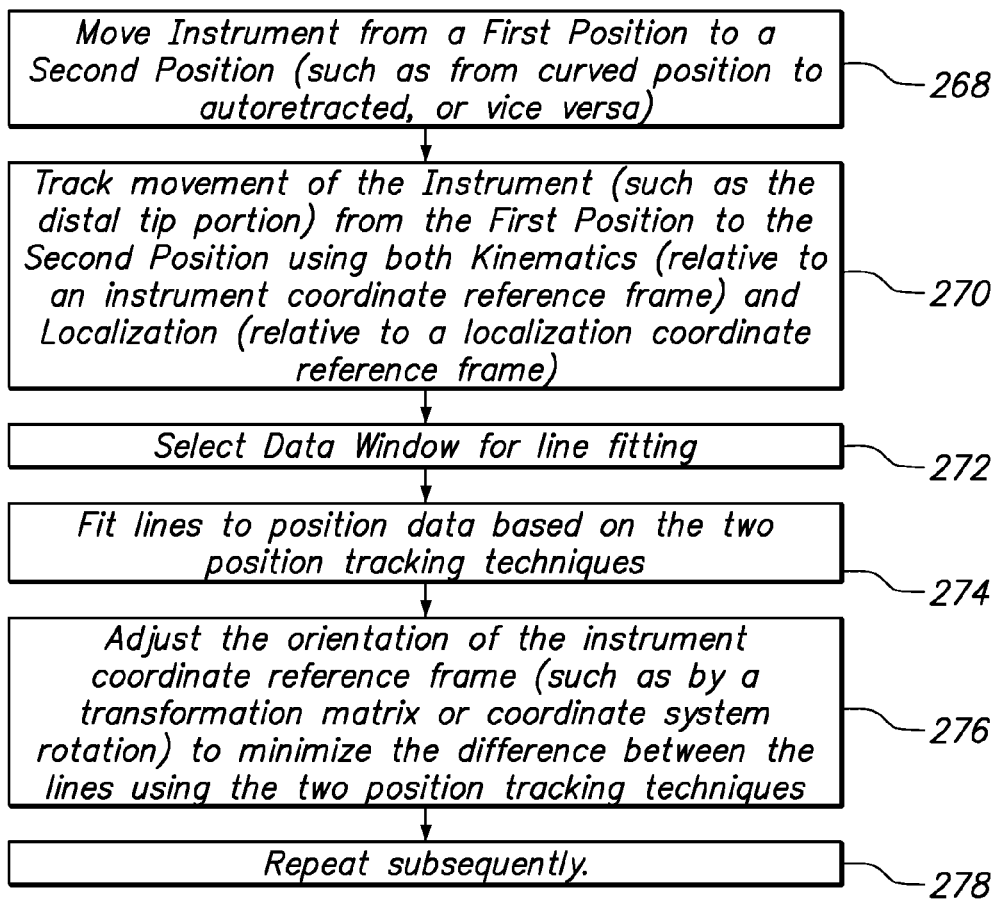
FIG. 6 illustrates one embodiment of a registration or alignment technique in accordance with the present invention.

Subsequent to having a reliable line fitted through each of the kinematic-based data and the localization-based data, an orientation difference between the kinematic-based data coordinate system (the instrument coordinate reference frame—48) and the localization-based data coordinate system (the localization coordinate reference frame—46) may be determined, and this difference may be treated as an error in the orientation of the instrument coordinate reference frame (48) which may be minimized by reorienting the instrument coordinate reference frame (48). Subsequent to such minimization, the two coordinate systems should be registered, "aligned", or "calibrated" relative to each other, and navigation of the instrument assembly (42) relative to the updated/reoriented instrument coordinate reference frame (48) should produce more predictable movements relative to other related coordinate systems and structures registered thereto. FIGS. 4-6 illustrate further aspects of registration embodiments.

Referring to FIG. 4, certain aspects of the aforementioned embodiment are summarized in a flowchart. A presumed roll orientation of the instrument coordinate reference frame may not be correct, or may need to be updated (250), due to the fact that if the roll orientation of the instrument coordinate reference frame is not correct, commanded movements may not result in movements exactly as desired (252). This registration challenge may be addressed by putting the instrument coordinate reference frame back into orientation alignment relative to the world coordinate system or other reliable coordinate reference frame (254), such as the localization coordinate reference frame (256).

Referring to FIG. 5, an instrument, such as an inner elongate instrument (81), may be moved from a first position to a second position. For example, the instrument may be moved from a retracted or autoretracted and substantially straight position, to a second position, such as a curved position (258). Alternatively, the instrument may be moved from a curved and relatively inserted position to a retracted or autoretracted and substantially straight position. In another variation, the instrument may simply be moved from one position to another, without retraction or autoretraction, such as in an embodiment wherein subtle cyclic motion is overlaid upon realtime navigational movement, allowing the system to be constantly cycling and analyzing new data, and constantly updating registration and alignment of the instrument coordinate reference frame (48) relative to other coordinate reference frames, such as a localization coordinate reference frame. Subsequent to determining orientations relative to the move trajectory in two different coordinate reference frames (262), orientation of the instrument coordinate reference frame (48) may be adjusted, such as by transformation matrix or coordinate system rotation, to minimize the difference between determined orientations using one position and coordinate system versus the other (264). Such a process may be repeated (266) periodically, constantly, once per procedure, after an incident wherein the instrument appears to be stuck on an adjacent structure, and the like.

Referring to FIG. 6, a flowchart similar to that depicted in FIG. 5 is shown, with additional details regarding the data windowing technique described above in reference to FIGS. 3A-3I. Referring to FIG. 6, an instrument or portion thereof may be moved from one position to another (268), the movement tracked in two different ways and two different coordinate reference frames (270). Acquired data from the movement tracking may be analyzed using data windowing (272), preferably wherein the window is made as inclusive as possible without violating a predetermined fitted line fit quality threshold. The lines fitted through the included data (274) may be compared, and the orientation of the instrument coordinate reference frame may be adjusted (276). As with the embodiment described in reference to FIG. 5, this process may be repeated intraoperatively (278).

Such registration embodiments may be broadly applied. For example, in one embodiment, they may be applied to an instrument configuration comprising a localized intravascular ultrasound ("IVUS") catheter coupled to another steerable catheter, such as through the working lumen of such steerable catheter. A localization sensor coupled to the IVUS catheter, and a kinematic model, may be used as described above to conduct movements and register the IVUS catheter and steerable catheter to various coordinate reference frames, to allow for coordinated, "instinctive" navigation relative to the coordinate systems of, for example, a master input device and/or display upon which IVUS and other images may be presented to the operator.

Having registered an instrument set to other pertinent coordinate systems and structures which are registered or aligned thereto, many intraoperative instrument coordination paradigms may be facilitated. Some of these are illustrated in FIGS. 7, 8, 9, and 10A-10C.

Figure 7:
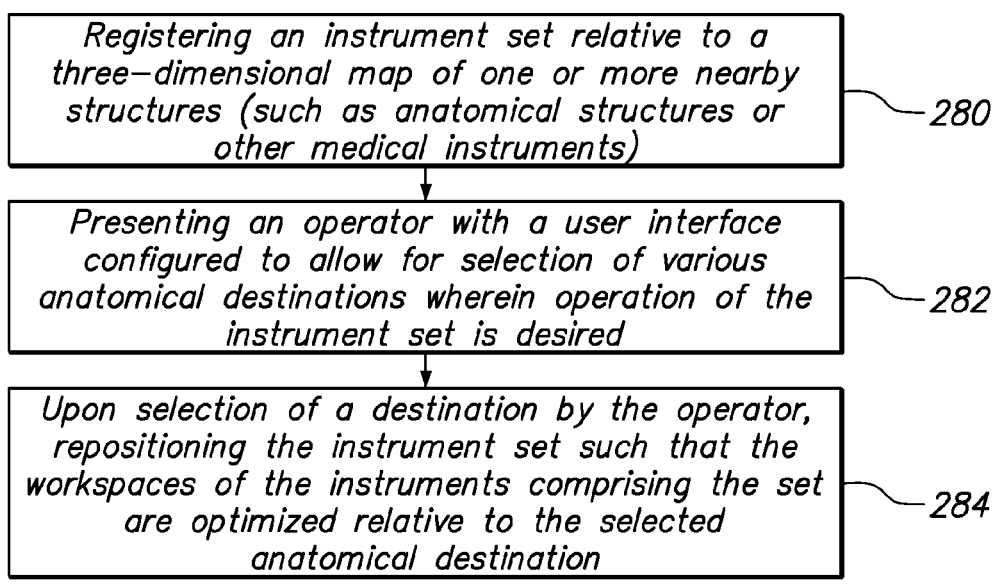
FIG. 7 illustrates one embodiment of a navigation configuration in accordance with the present invention.

Referring to FIG. 7, subsequent to registering an instrument set relative to a three dimensional map of one or more nearby structures, such as anatomical structures or other medical instruments or foreign bodies (280), an operator may be presented with a user interface configured to allow for operator selection of various anatomical destinations wherein operation of the instrument set is desired (282). For example, having positioned an instrument set in the inferior vena cava and confirmed registration to a reliable coordinate system such as a localization coordinate system, an operator may utilize a software-based (such as menus, or manual selection using a master input device and an anatomical map displayed for the operator) or hardware based (for example, buttons on a pendant or keyboard hardware device) controls to select a trans-atrial-septal approach, after which the system may be configured to move/reposition the instrument set such that the workspaces of the instruments are optimized (284) relative to the selected anatomical destination (in one transseptal embodiment, with the outer instrument distal tip positioned substantially perpendicular to the atrial septal wall, and with the inner instrument workspace positioned to allow movement of the inner instrument as far across the atrial septal wall as possible given the limits of the inner instrument workspace). In other words, the system may be preconfigured to assist the operator in optimally positioning a registered instrument set for certain predetermined intraoperative procedures or portions thereof.

Figure 8:
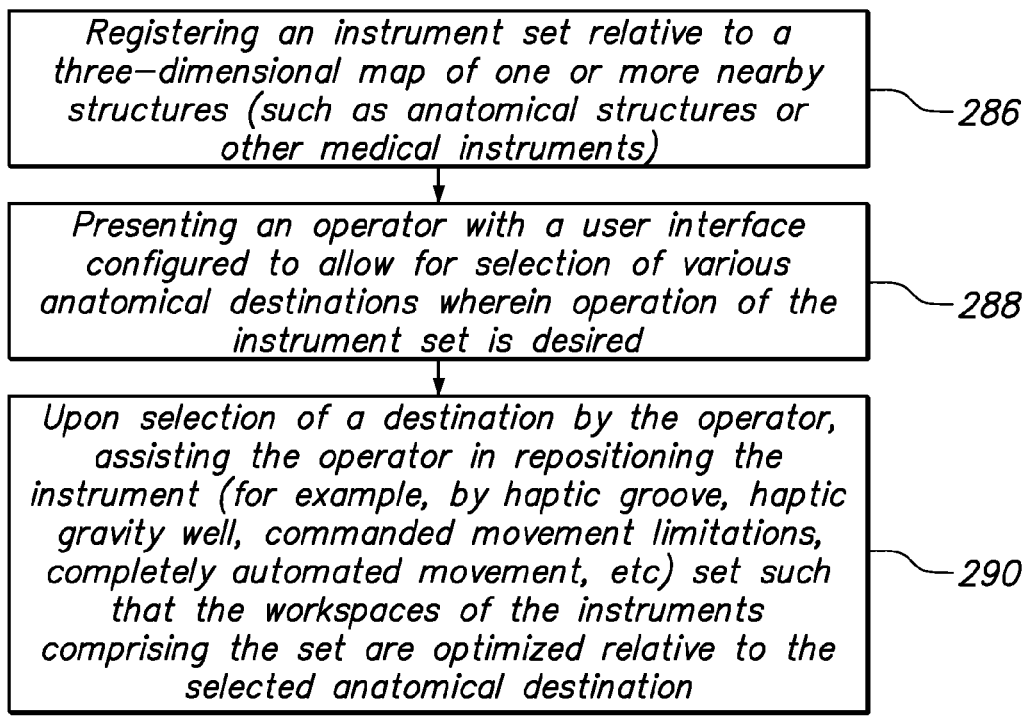
FIG. 8 illustrates one embodiment of a navigation configuration in accordance with the present invention.

Referring to FIG. 8, another similar embodiment is illustrated wherein after registration (286) and selection (288), rather than fully automated movement of the instrument set, as in the embodiment described in relation to FIG. 7, the embodiment of FIG. 8 is configured to assist (290) the operator's repositioning of the instrument, using techniques such as guiding navigation of the instrument using a haptic master input device and a haptic groove or haptic gravity well. In other variations, movement may be limited by the system to avoid predetermined zones of preferred minimal or zero contact, to move only along a curve or line or within a plane, and the like—all to position the instrument set in a configuration optimized for the preselected anatomical destination.

Figure 9:
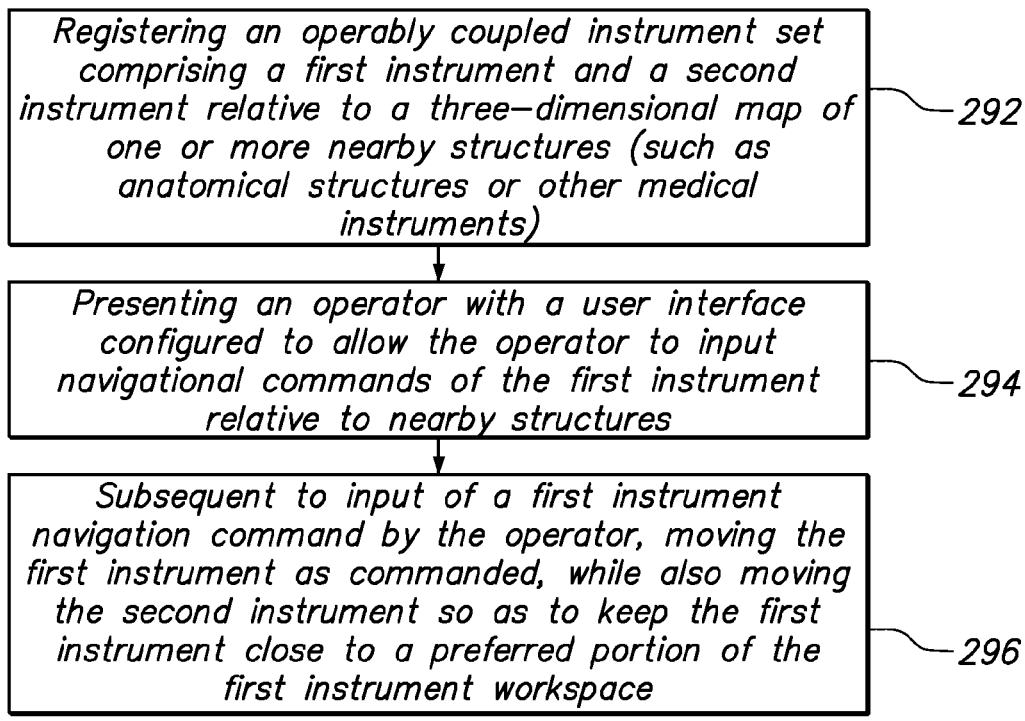
FIG. 9 illustrates one embodiment of a navigation configuration in accordance with the present invention.

Referring to FIG. 9, another embodiment is illustrated wherein after registering (292) an operably coupled instrument set to a three-dimensional map of one or more nearby structures, such as anatomical structures, other medical instruments, foreign bodies, and the like, the operator may be presented with a navigation mode wherein commands input (294), for example, at a master input device, may be utilized by the system to assist in optimal positioning of the instrument workspace of the first instrument (296) through automated repositioning of the second instrument. In other words, if the system interprets through an issued movement command from an operator that the operator wishes to take at least a portion of the first instrument, such as the inner instrument (81) to a certain location, the system may be configured to move not only the first instrument, but also the second operatively intercoupled instrument, such as the outer instrument (79), to place the first instrument workspace optimally. In the illustrated embodiment, such optimal positioning comprises moving the second instrument so as to keep the first instrument close to a preferred portion of the first instrument workspace, such as at the center of such workspace. In another embodiment, the second instrument may be moved so as to keep the first instrument close to the preferred portion of the workspace of the first instrument only after the first instrument crosses a threshold of misalignment with the preferred portion of the workspace. For example, with such an embodiment, the second instrument would remain in position until the first instrument reaches, say, 80% of the way (i.e., an 80% threshold) to its instrument workspace, after which the second instrument would move to assist positioning of the first instrument closer to the center of its workspace. Such embodiments may be configured to keep one instrument in the center of its workspace, in a forward oriented conical volume known to be easiest for the instrument to accurately and expediently navigate, etcetera.

Figure 10A:
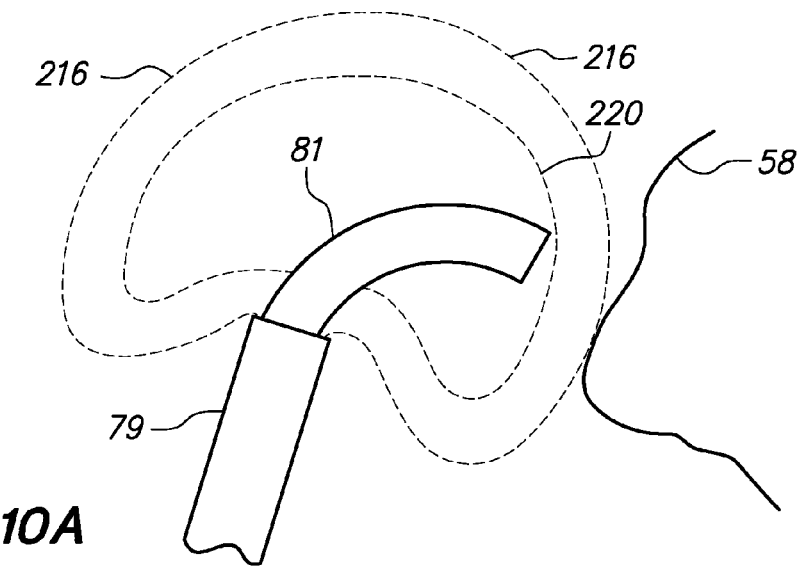
FIGS. 10A-10C illustrate one embodiment of a navigation configuration in accordance with the present invention.
Figure 10B:
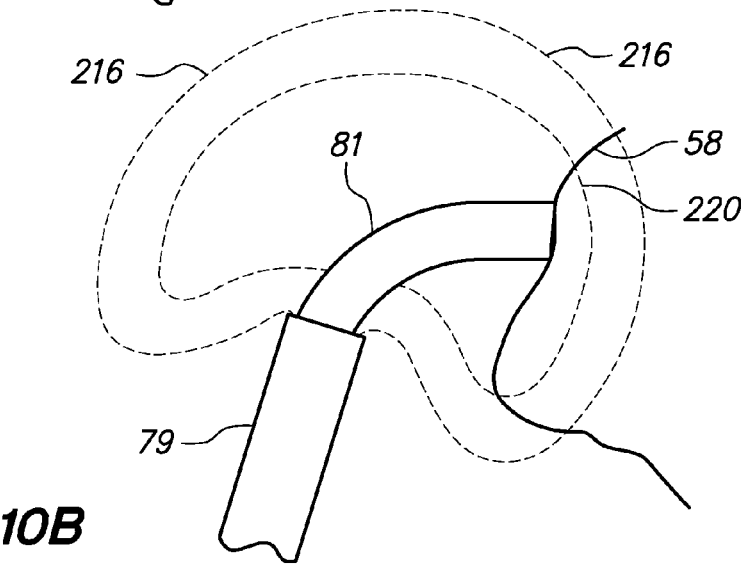
Figure 10C:
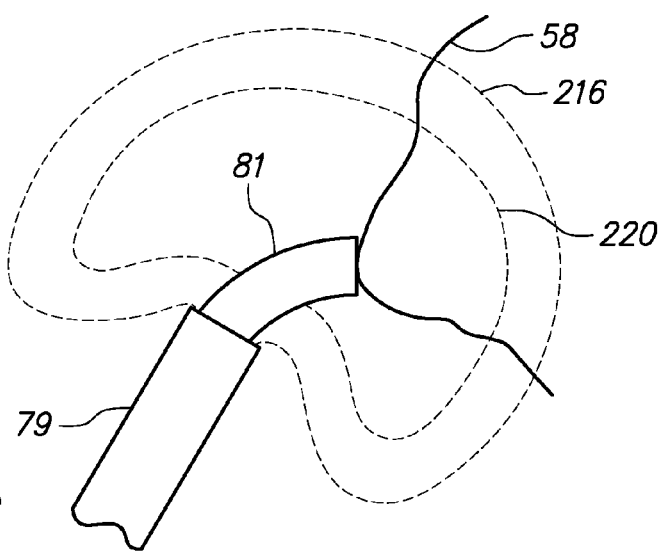

Referring to FIGS. 10A-10C, a related embodiment is depicted. As shown in FIG. 10A, an inner instrument (81) is being advanced toward a tissue structure (58). As the inner instrument (81) crosses an instrument workspace (216) threshold (an imaginary line depicted as element 220; in some embodiments this imaginary line may be presented to the operator in the user interface), as in FIG. 10A, the outer instrument (79) moves over toward the targeted tissue structure (58), thereby carrying the inner instrument with it, along with the inner instrument's workspace, which is shown in FIG. 10B as advanced over to the right toward the targeted tissue structure (58). In one embodiment, the outer instrument may be configured to advance over, or "swallow" over, the proximal exposed portion of the inner instrument to further increase stability and, depending upon the available remaining room in the insertion degree of freedom, to continue to advance the inner instrument (81) workspace (216) toward the targeted tissue structure.

In another embodiment, a shape representing the desired region of the second instrument's workspace may be modeled as an implicit surface, and rendered haptically using haptic implicit surface algorithms—and the direction of the resultant force may be used as the direction in which to move the first instrument. Such force direction may be altered if the motion of the first instrument is desired to be constrained in some way; for example, in one embodiment, it may be projected onto an instrument roll plane to prevent adding torque.

While multiple embodiments and variations of the many aspects of the invention have been disclosed and described herein, such disclosure is provided for purposes of illustration only. For example, wherein methods and steps described above indicate certain events occurring in certain order, those of ordinary skill in the art having the benefit of this disclosure would recognize that the ordering of certain steps may be modified and that such modifications are in accordance with the variations of this invention. Additionally, certain of the steps may be performed concurrently in a parallel process when possible, as well as performed sequentially. Accordingly, embodiments are intended to exemplify alternatives, modifications, and equivalents that may fall within the scope of the claims.

The invention claimed is:

1. A method for registering an elongate medical instrument relative to nearby anatomical structures, comprising:
moving a distal portion of a robotically controlled elongate medical instrument between a first position in situ and a second position in situ relative to an instrument coordinate reference frame, wherein the elongate medical instrument is coaxially positioned through a working lumen of a robotically-controlled sheath instrument, and wherein respective robotic movement of the medical and sheath instruments is controlled by a processor operatively coupled to the respective medical and sheath instruments, wherein the processor
tracks movement of the distal portion of the medical instrument relative to the instrument coordinate reference frame using respective kinematic models for the medical and sheath instruments,
tracks movement of the distal portion of the medical instrument relative to a localization coordinate reference frame using one or more localization sensors coupled to the distal portion of the medical instrument,
determines the orientation of the instrument distal end portion relative to both the instrument coordinate reference frame and the localization coordinate reference frame, and
adjusts the orientation of the instrument coordinate reference frame to minimize the difference between determined orientations using the kinematic models and localization sensors.

2. The method of claim 1, wherein the first position in situ is a substantially straight position for the distal portion of the medical instrument.

3. The method of claim 2, wherein in the first position in situ, the distal portion is medical instrument is substantially coincident with a coordinate axis representing a substantially unloaded, substantially straight, longitudinal axis of the distal portion of the medical instrument.

4. The method of claim 1, wherein the distal portion of the medical instrument has been retracted toward the working lumen of the sheath instrument with the sheath instrument in a substantially straight position in the first position in situ.

5. The method of claim 1, wherein the first position in situ is achieved with an electromechanical autoretraction command.

6. The method of claim 1, wherein the processor tracks movement of the distal portion of the medical instrument relative to the instrument coordinate reference frame by determining an estimated position of the distal portion of the medical instrument based at least in part upon an insertion position of the portion of the medical instrument and positions of one or more steering positioners comprising the medical instrument.

7. The method of claim 6, wherein the elongate medical instrument is a steerable catheter, and wherein the one or more steering positioners comprise steering pullwires.

8. The method of claim 1, wherein the one or more localization sensors are potential difference based localization sensors.

9. The method of claim 1, wherein the one or more localization sensors are magnetic field based localization sensors.

10. The method of claim 1, wherein the second position in situ is a curved position for the distal portion of the medical instrument.

11. The method of claim 10, wherein the curved position has a minimum radius of curvature, and wherein a user interface is configured to assist an operator in positioning the distal portion of the medical instrument into a curved position having a radius of curvature greater than or equal to the minimum radius of curvature.

12. The method of claim 11, wherein the user interface presents the operator with a cylindrical shaped guiding envelope past which the medical instrument distal portion should be driven to place the portion into a curved position having a radius of curvature greater than or equal to the minimum radius of curvature.

13. The method of claim 1, wherein the processor determines the orientation of the medical instrument distal portion relative to the localization coordinate reference frame by selecting a subset of available localization data collected for movement of the medical instrument distal portion between the first position in situ and the second position in situ, fitting a line through the subset, and determining orientation relative to the localization coordinate reference frame based upon the position of the line.

14. The method of claim 13, wherein selecting a subset of available localization data comprises fitting a line through an initial subset of available localization data collected for movement of the medical instrument distal portion between the first position in situ and the second position in situ, the initial subset being one that is presumed to contain data that is less likely to be noisy.

15. The method of claim 14, further comprising sequentially
a) adding additional data from the available localization data collected to form an updated subset of data;
b) fitting a line through the updated subset of data;
c) determining the quality of fit of the line through the updated subset of data; and
d) determining, based upon the quality of fit, an optimized subset of data for determining the orientation of the medical instrument distal portion relative to the localization coordinate reference frame.

16. The method of claim 15, wherein determining the quality of fit comprises determining the root mean square error of data comprising the updated subset of data relative to the line fitted through such data.

17. The method of claim 1, wherein moving a distal portion of the medical instrument between a first position in situ and a second position in situ is conducted as an overlay to other concurrent navigation of the medical instrument.

18. The method of claim 1, further comprising stopping other navigation of the medical instrument before initiating the moving of the distal portion of the medical instrument between a first position in situ and a second position in situ.

19. The method of claim 1, wherein an IVUS imaging assembly is coupled to the medical device, and wherein the processor takes into account image data acquired by the IVUS imaging assembly for tracking movement of the distal portion of the medical device.

20. The method of claim 19, further comprising allowing for an operator adjustment of the orientation of the instrument coordinate reference frame, and synchronizing adjustment of an associated master input device coordinate reference frame to retain instinctiveness of the master input device relative to observed operation of the elongate medical device.

21. A system for registering an elongate medical instrument relative to nearby anatomical structures, comprising:
a. a remotely navigated working elongate medical instrument having a distal end, an elongate body, and one or more localization sensors coupled to the elongate body;

b. a remotely navigated secondary instrument having a working lumen configured to slidably engage the elongate medical instrument;

c. a localization system coupled to the one or more localization sensors and configured to determine the positions of such sensors relative to a localization coordinate reference frame;

d. a processor operatively coupled to the working elongate medical instrument and secondary instrument, and configured to determine the position thereof relative to an instrument coordinate reference frame based upon kinematic models for the instruments;

wherein the processor is configured to:
1) move a portion of the working elongate medical instrument between a first position in situ and a second position in situ relative to the instrument coordinate reference frame;
2) track movement of the portion relative to the instrument coordinate reference frame using a kinematic model, and also tracking movement of the portion relative to a localization coordinate reference frame using one or more localization sensors coupled to the portion;
3) determine the orientation of the portion relative to both the instrument coordinate reference frame and the localization coordinate reference frame; and
4) adjust the orientation of the instrument coordinate reference frame to minimize the difference between determined orientations using the kinematic model and localization sensors.

22. The system of claim 21, wherein the working elongate medical instrument is a flexible catheter.

23. The system of claim 21, wherein the secondary instrument is a flexible sheath catheter.

24. The system of claim 22, wherein the flexible catheter is a robotically steerable catheter, and wherein the processor is configured to move the catheter between a first position and a second position electromechanically.

25. The system of claim 21, wherein the processor is configured to track movement of the portion using a kinematic model by determining an estimated position of the portion based at least in part upon an insertion position of the portion and positions of one or more steering positioners comprising the elongate medical instrument.

26. The system of claim 25, wherein the one or more steering positioners comprise steering pullwires.

27. The system of claim 21, wherein the one or more localization sensors are potential difference based localization sensors.

28. The system of claim 21, wherein the one or more localization sensors are magnetic field based localization sensors.

29. The system of claim 21, wherein the first position is a substantially straight position, and the second position is a curved position wherein the portion has a radius of curvature greater than or equal to a threshold minimum radius of curvature.

30. The system of claim 29, wherein the processor is configured to assist an operator in positioning the portion into the curved position.

31. The system of claim 30, wherein the processor directs a user interface to present to the operator a cylindrical shaped guiding envelope past which the elongate instrument portion should be driven to place the portion into a curved position having a radius of curvature greater than or equal to the minimum radius of curvature.

32. The system of claim 24, wherein the processor is configured to autoretract the catheter between a first position and a second position electromechanically.

* * * * *

UNITED STATES PATENT AND TRADEMARK OFFICE
CERTIFICATE OF CORRECTION

PATENT NO. : 8,317,746 B2
APPLICATION NO. : 12/507777
DATED : November 27, 2012
INVENTOR(S) : Sewell et al.

Page 1 of 1

It is certified that error appears in the above-identified patent and that said Letters Patent is hereby corrected as shown below:

At Column 13, Claim 3, line 38, "portion is medical" should read:

--portion of the medical--

At Column 13, Claim 6, line 54, "of the portion" should read:

--of the distal portion--

Signed and Sealed this
Fifth Day of March, 2013

Teresa Stanek Rea
*Acting Director of the United States Patent and Trademark Office*